US010888265B2

(12) United States Patent
Edwards

(10) Patent No.: US 10,888,265 B2
(45) Date of Patent: Jan. 12, 2021

(54) JAW FUNCTION MEASUREMENT APPARATUS

(71) Applicant: Donna Edwards, Dayton, OH (US)

(72) Inventor: Donna Edwards, Dayton, OH (US)

( * ) Notice: Subject to any disclaimer, the term of this patent is extended or adjusted under 35 U.S.C. 154(b) by 254 days.

(21) Appl. No.: 15/287,282

(22) Filed: Oct. 6, 2016

(65) Prior Publication Data
US 2017/0100069 A1    Apr. 13, 2017

Related U.S. Application Data

(60) Provisional application No. 62/238,696, filed on Oct. 7, 2015.

(51) Int. Cl.
*A61B 5/22*    (2006.01)
*A61B 5/11*    (2006.01)
*A61B 5/00*    (2006.01)

(52) U.S. Cl.
CPC .............. *A61B 5/228* (2013.01); *A61B 5/11* (2013.01); *A61B 5/7246* (2013.01); *A61B 2562/0252* (2013.01); *A61B 2562/04* (2013.01); *A61B 2562/06* (2013.01)

(58) Field of Classification Search
CPC ............... A61B 5/682; A61B 5/228; A61B 5/4542–4557; A61B 5/7246; A61B 5/11; A61C 19/045; A61C 19/05
USPC ........................................................ 600/590
See application file for complete search history.

(56) References Cited

U.S. PATENT DOCUMENTS

| | | | |
|---|---|---|---|
| 5,609,161 A | 3/1997 | Tura et al. | |
| 6,089,864 A * | 7/2000 | Buckner | A61F 5/56 |
| | | | 433/6 |
| 6,098,627 A * | 8/2000 | Kellner | A61C 5/90 |
| | | | 128/859 |
| 7,890,193 B2 | 2/2011 | Tingey | |
| 7,914,468 B2 | 3/2011 | Shalon et al. | |
| 2002/0032392 A1* | 3/2002 | Kato | A61B 5/14551 |
| | | | 600/590 |
| 2004/0073142 A1* | 4/2004 | Takeuchi | A61B 5/0088 |
| | | | 600/595 |
| 2006/0237020 A1* | 10/2006 | Morgan | A63B 71/085 |
| | | | 128/862 |

(Continued)

FOREIGN PATENT DOCUMENTS

WO    2015/104683 A2    7/2015

OTHER PUBLICATIONS

Lantada, A. D. et al.; "Novel System for Bite-Force Sensing and Monitoring Based on Magnetic Near Field Communication"; Sensors; 2012.

(Continued)

*Primary Examiner* — Daniel L Cerioni
(74) *Attorney, Agent, or Firm* — Thomas E. Lees, LLC

(57) ABSTRACT

A jaw function measurement apparatus comprises a mastication measurement device having a pliable body, the pliable body defining at least one bite location having at least one force sensor therein. A data collection device is in data communication with the mastication measurement device. Also, a data analysis device is in data communication with the data collection device, which converts data collected by the data collection device into a format suitable for output. Moreover, an input output device is in data communication with the data analysis device 106 that outputs measured bite force.

19 Claims, 10 Drawing Sheets

(56) References Cited

U.S. PATENT DOCUMENTS

| | | | |
|---|---|---|---|
| 2008/0010080 A1* | 1/2008 | Torney | A23K 50/40 705/1.1 |
| 2008/0183107 A1 | 7/2008 | Miller et al. | |
| 2010/0036286 A1* | 2/2010 | Scholz | A61B 5/0002 600/590 |
| 2011/0125063 A1* | 5/2011 | Shalon | A61B 5/1112 600/590 |
| 2011/0178550 A1 | 7/2011 | Tesini et al. | |
| 2011/0190666 A1 | 8/2011 | Friedland et al. | |
| 2011/0276312 A1 | 11/2011 | Shalon et al. | |
| 2013/0042876 A1* | 2/2013 | Hermanson | A61F 5/566 128/848 |
| 2013/0296751 A1 | 11/2013 | Martin et al. | |
| 2015/0305669 A1* | 10/2015 | Hultgren | A61B 5/4547 433/27 |

OTHER PUBLICATIONS

Simone Guimaraes Farias Gomes et al.; "Chewing Side, Bite Force Symmetry, and Occlusal Contact Area of Subjects with Different Facial Vertical Patterns"; Brazilian Oral Research; vol. 25, No. 5; Sep./Oct. 2011.

Laine, C. M. et al.; "Jaw Tremor as a Physiological Biomarker of Bruxism"; Clinical Neurophysiology; 2014.

McGarry, J. et al.; "Dynamic Evaluation of Forces During Mastication"; Worcester Polytechnic Institute; downloaded Oct. 1, 2015.

Singh, S. et al.; "An Innovative Miniature Bite Force Recorder"; Jaypee Journals; International Journal of Clinical Pediatric Dentistry; May-Aug. 2011.

Sazonov, E. et al.; "Non-Invasive Monitoring of Chewing and Swallowing for Objective Quantification of Ingestive Behavior"; HHS Public Access; Physiol Meas.; May 2008.

Yamasaki, Y. et al.; "Objective Assessment of Actual Chewing Side by Measurement of Bilateral Masseter Muscle Electromyography"; Archives of Oral Biology; vol. 60, issue 12; Dec. 2015.

Ono, T. et al.; "Recent Advances in Sensing Oropharyngeal Swallowing Function in Japan"; Sensors; 2010.

Tamilia, E. et al.; "Technological Solutions and Main Indices for the Assessment of Newborns' Nutritive Sucking: A Review"; Sensors; 2014.

Tekscan; "Bite Force Measurement"; Introducing T-Scan® Novus™; Tekscan, Inc.; downloaded on Oct. 1, 2015.

* cited by examiner

| 702 | 704 | 706 | 708 | 710 | 712 | 714 | 716 |
|---|---|---|---|---|---|---|---|
| NO BITE | BITE | FREQUENCY | DURATION | ENDURANCE | SHEAR | JAW POSITION | HARDNESS |
| Y/N | FORCE APPLIED | FORCE TREND AT TIME BETWEEN BITES | TIME LENGTH OF BITE (HOW LONG FORCE APPLIED PER BITE) | HOW LONG/HOW MANY (COUNT) OF REPEATED BITES (CHEWING ACTION) | FORCE APPLIED TRANSVERSE TO BITE FORCE | THICKNESS | RIGIDITY |

JAW FUNCTION MEASUREMENT APPARATUS

CROSS REFERENCE TO RELATED APPLICATIONS

This application claims the benefit of U.S. Provisional Patent Application Ser. No. 62/238,696, filed Oct. 7, 2015, entitled JAW FUNCTION MEASUREMENT APPARATUS, the disclosure of which is hereby incorporated herein by reference.

BACKGROUND

Various aspects of the present disclosure relate generally to jaw function measurement, and more particularly to a jaw function measurement apparatus capable of graded analysis of jaw function.

Mastication (chewing) requires the interaction of several muscle groups, the mechanics of which are refined during growth and development into a subconscious task that many individuals take for granted. However, certain individuals struggle to develop this fundamental functionality. In developed individuals, mastication is carried out using a combination of clenching and grinding motions. The clenching motion enables individuals to use their incisors to shear bites from food. The clenching motion also enables individuals to use their molars to compress the bite of food. Similarly, the grinding motion enables individuals to use their molars to apply a combination of compression and shear forces to the bite of food. As such, these clenching and grinding motions are important skills to enable an individual to properly swallow and subsequently digest food.

BRIEF SUMMARY

According to aspects of the present disclosure, a jaw function measurement apparatus comprises a mastication measurement device having a pliable body, the pliable body defining at least one bite location having at least one force sensor therein. A data collection device is in data communication with the mastication measurement device. Also, a data analysis device is in data communication with the data collection device, which converts data collected by the data collection device into a format suitable for output. Moreover, an output device is in data communication with the data analysis device that outputs measured bite force.

BRIEF DESCRIPTION OF THE SEVERAL VIEWS OF THE DRAWINGS

FIG. 7 is an example set of parameters that define various measurements that can be collected by the jaw function measurement apparatus of FIG. 1;

DETAILED DESCRIPTION

Chewing skills classically emerge as young children are teething. Biting on various food surfaces with sufficient skill optimizes dental eruption and enhances the development of chewing function. However, some children do not develop the proper mechanics to chew properly. Moreover, adolescent and adult individuals can experience disruptions in the ability to chew as a result of injuries, disease, or other conditions. One approach specialists use to detect abnormalities in chewing skill is through the assessment of jaw function, which can serve as a measure of the individual's ability to perform the clenching and grinding motions necessary to chew food. Unfortunately, previous attempts to assess jaw function, particularly in the pediatric population, have been unsuccessful because known prior techniques to assess jaw function rely upon subjective assessments based upon the specialist's observation alone.

However, according to aspects of the present disclosure, a jaw function measurement apparatus is provided. The jaw function measurement apparatus enables objective data to be collected and analyzed. More particularly, the jaw function measurement apparatus provides repeatable and accurate measurement of jaw function by collecting data on bite force and chewing patterns of individuals. Jaw function data collected by the jaw function measurement apparatus can be used, for instance, to objectively assess feeding skill development. Also, jaw function data can be collected by the jaw function measurement apparatus on typically developmental pediatric populations. This collected data can be used to enhance and provide baseline data to optimize clinical assessment and treatments of chewing skill development in children with atypical feeding development skills. Still further, jaw function data collected by the jaw function measurement apparatus can provide the necessary analytic data to a specialist in order to assist an individual towards a transition to foods requiring increased repetitive chewing and bite force. Increasing chewing function may reduce choking risk in the pediatric population, especially in the higher risk group of children from ages one to four.

Figure 1:
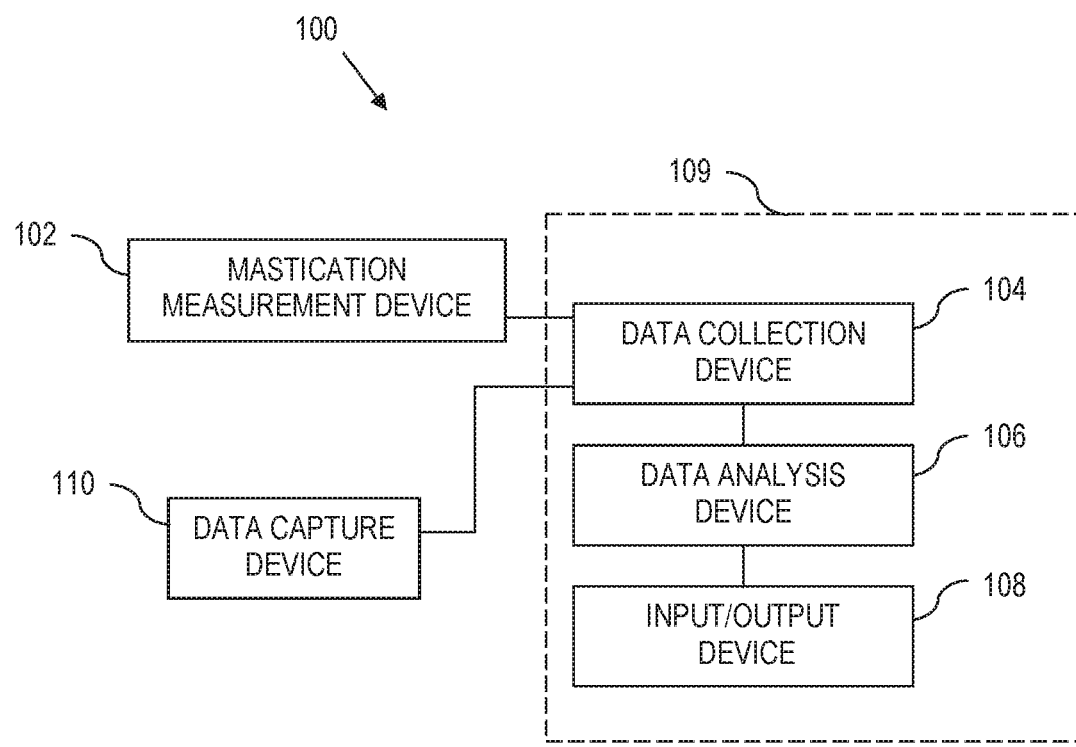
FIG. 1 is a block diagram of an example jaw function measurement apparatus.

Referring to the drawings and in particular FIG. 1, a jaw function measurement apparatus 100 is provided. The jaw function measurement apparatus 100 comprises in general, a mastication measurement device 102, a data collection device 104, a data analysis device 106, and an input/output device 108. The data collection device 104 is in data communication with the mastication measurement device 102 to receive and record measurements captured by the mastication measurement device 102. The data analysis device 106 is in data communication with the data collection device 104 and is provided to convert data collected by the data collection device 104 into a format suitable for output. The input/output device 108 is in data communication with the data analysis device 106 to output the measured parameters associated with jaw function. The input/output device 108 can also connect to the data collection device 104, the data analysis device 106, or both to provide inputs, such as to configure specific measurements, initiate measurement activities, configure user interface settings, configure output settings, etc.

In a first illustrative example implementation, the data collection device 104, the data analysis device 106, and the input/output device 108 are combined in a single physical unit 109, e.g., a hand-held or otherwise portable device. In an alternative example implementation, the data analysis device 106 and/or the input/output device 108 can be implemented in a device separate from the data collection device 104. For instance, the data collection device 104 can include a hand-held or otherwise portable device that collects data from the mastication measurement device 102. The data is then dumped at some point after collection, e.g., either via a wired connection or wireless connection, to a processing device, e.g., a computer having a processor that executes computer code stored in memory to implement the data analysis device 106. The computer can also include hardware and/or software necessary to implement the input/output device 108. In this example, the input/output device 108 can be implemented by a graphical user interface executed by the computer, by a combination of components, e.g., display, keyboard, mouse, network adapter, portable memory drive, combination thereof, etc.

As will be described in greater detail herein, the mastication measurement device 102 is used to measure jaw function, typically through bite-related data. Bite-related data thus includes data that characterizes biting, chewing, jaw functionality, or combinations thereof of individuals being evaluated.

For instance, in an example implementation, the mastication measurement device 102 includes at least one force sensor that is operatively configured to measure force in at least one direction. In certain example implementations, the mastication measurement device 102 includes multiple sensors, each arranged in one or multiple orientations, patterns, or otherwise, to achieve the desired bite-related data. Here, each sensor can be a force sensor or other type of sensor.

An example sensor other that a force sensor comprises a vibration sensor. The vibration sensor provides a natural transition during treatment and may increase use of device functionally. Another example sensor is a temperature generating sensor (e.g., a sensor capable of generating cold or heat.) The temperature generating sensor enables the use of warm and cool temperatures in therapy as well as to help certain patients (such as those with autism) transition to different food temperatures (warm to cool). In this regard, the temperature generating sensor can include at least one heating element, at least one cooling element, a combination thereof, etc.

In this regard, bite-related data can represent information directly measured from the mastication measurement device 102, or data that is otherwise derived based upon one or more measurements from the mastication measurement device 102 (e.g., via computation by the data analysis device 106). Derived data can utilize one or more variables, including for instance, force measurements from one sensor or a combination of sensors from the mastication device 102, time measurements, temperature measurements, duration/interval measurements, counts of force above a predetermined threshold, a combination thereof, etc.

By way of illustration, the bite-related data generated by the jaw function measurement apparatus 100 can represent one or more of parameters including an indication of a willingness/ability to bite, measured bite force, measured chew frequency (including time between successive bites), measured bite duration (e.g., the length of time that the bite is clenched down—how long force is applied during a bite), measured chew endurance (length in time or chew count of sustainable repetitive bites), measured shear force (force transverse to bite force), etc. These parameters can be combined or otherwise manipulated further to derive chewing patterns, chewing trends, bite patterns, bite trends, other measurements, combinations thereof, etc.

The data collection device 104 receives data from the mastication measurement device 102. In this regard, the data collection device 104 can store data, archive data, retrieve data, condition data, etc., which is received from the mastication measurement device 102. Moreover, in certain embodiments, the data collection device 104 can tether to the mastication measurement device 102 via wired or wireless connection to supply inputs, to read measurements, to execute data collection algorithms such as timed data collection activities, to execute programmed tests, etc. In this regard, the mastication measurement device 102 and the data collection device 104 each include necessary circuitry to carry out communication therebetween.

The data analysis device 106 performs data aggregation, processing, statistical data analysis, combinations thereof, etc., of discrete parameters or simultaneously collected parameters that are recorded by the mastication measurement device 102. In this regard, processes performed by the data analysis device 106 can utilize historical data collected for the same individual being evaluated. The data analysis device 106 can also use averages, benchmarks, trends, thresholds, measurements, and other parameters that are derived across one or more groups that have been tested using the jaw function measurement apparatus 100 described herein.

As will be described in greater detail herein, the jaw function measurement apparatus 100 can include a plurality of mastication measurement devices 102, e.g., each varying in thickness to allow graded analysis of jaw function by requiring the jaw to initiate the onset of a bite with the jaw in different angular positions. This allows the same or different tests to be performed, each time re-orienting the jaw to a different angular position at the onset of a bite. Moreover, various mastication measurement devices 102 can have different material rigidity, making it harder (relatively more rigid material) or easier (relatively softer material) to bite into the mastication measurement device 102. As a further example, a single mastication measurement device 102 can have more than one thickness, various positions with different rigidity, combinations thereof, etc. This example jaw function measurement apparatus 100 facilitates at least two measurement sections having different thicknesses selected to define a measure of jaw function, e.g., which can be utilized to assess the development of proper chewing technique.

Accordingly, the data analysis device 106 can assess chewing function by evaluating measurement data across a gradation of jaw function measurements (i.e., collect measurements in several different jaw positions). The data analysis device 106 also allows for the generation of an electronic report. As a few illustrative examples, a report can be generated to reflect baseline data, progress in therapy, discharge criteria with consideration of parent/caregiver/ patient goals/objectives, learned negative behavioral responses, negative physiological responses, hypergag response data, impulsivity, structural limitations, choking risk, combinations thereof, etc. As an additional example, an evaluation or re-assessment report can be generated.

At least one optional additional data capture device 110, e.g., a camera, video device, scanning device, ear canal recording device, device capable of capturing kinematic data, etc., can be used to capture data concomitantly with the data collection by the mastication measurement device 102. This allows the specialist to evaluate data in addition to bite-based data. For instance, in an example embodiment, the data analysis device 106 receives data from the mastication measurement device 102 and the optional data capture device 110 (e.g., either directly or via the data collection device 104), and can merge, perform data fusion, augment, time align, convert, perform combinations thereof, etc., the various data. This may provide greater insights into atypical bite and chew behaviors. For instance, an optional data capture device 10 such as a camera can capture images/video of jaw movement, which can be combined with bite data to better extract meaning to the collected data. In practice, multiple additional data capture devices 110 can be utilized to simultaneously capture different data sets to augment the data collected by the mastication measurement device 102.

Figure 2:
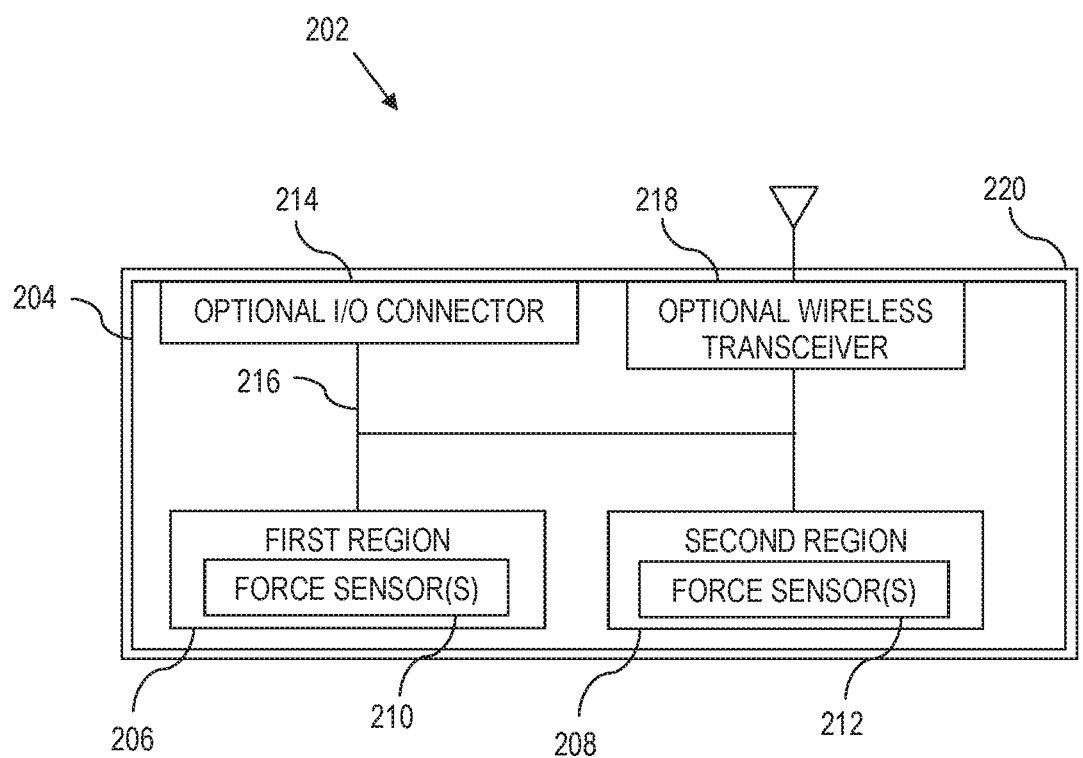
FIG. 2 is a block diagram of an example mastication measurement device.

Referring to FIG. 2, a mastication measurement device 202 is schematically illustrated. Unless otherwise noted, the mastication measurement device 202 is analogous to, and includes the same features of the mastication measurement device 102 of FIG. 1.

In the example implementation, the mastication measurement device 202 includes a body 204 that defines at least two distinct regions. Solely for sake of simplified explanation, the illustrated mastication measurement device 202 includes a first region 206 and a second region 208. The second region 208 is thicker than the first region 206. As noted above, the first region 206 can have the same material rigidity as the second region 208, or the rigidity/stiffness can be different. This enables two distinct measurements of chewing capability of an individual under examination from the same device. Of course, as noted above, the mastication measurement device 202 need not include multiple distinct sensor regions. In order to collect data, the mastication measurement device 202 includes at least one force sensor 210 within the first region 206. Likewise, the mastication measurement device 202 includes at least one force sensor 212 within the second region 208.

In practice, the mastication measurement device 202 is not limited to two regions 206, 208. Rather, there can be a plurality of widths (thicknesses) each with one or more sensors for the assessment of varying jaw positions with a single mastication measurement device 202. Likewise, material rigidity can be uniform throughout the bite region (s), or rigidness can vary across two or more bite regions to further provide flexibility in testing.

In an example implementation where the mastication measurement device 202 is wired to a corresponding data collection device, the mastication measurement device 202 includes an input/output connector 214. A bus 216 connects each force sensor 210 in the first region 206 and each force sensor 212 in the second region 208 to the input output connector 214.

In an alternative example implementation, the mastication measurement device 202 includes a wireless transceiver 218 that is connected to the bus 216. The wireless transceiver 218 can be implemented in Bluetooth or other suitable wireless technology.

In yet additional embodiments, the mastication measurement device 202 can include both the input/output connector 210 and the wireless transceiver 216 to provide multiple alternative ways to pass data from the mastication measurement device 202 to a corresponding data collection device, e.g., the data collection device 104 of FIG. 1.

As will be described in greater detail below, the various embodiments of mastication measurement device herein can incorporate sensors along multiple contact points to collect quantifiable data regarding function and development of skills. The shape of the sensors can be narrow so as to allow a form factor that will fall along the molars or molar ridges of the individual being tested. For instance, in an example implementation, the mastication measurement device shape is elongated but narrow for best alignment with a gum line (molar ridge) or molars of the individual being evaluated.

Still further, in certain embodiments, shear forces (transverse to bite force) can be measured, e.g., by detecting or measuring a change in deflection along a prescribed measurement region of the mastication measurement device 202.

Moreover, in illustrative implementations, the mastication measurement device 202 allows a position for an evaluator/clinician to hold and to maintain control of the mastication measurement device 202 (e.g., via a handhold, handle or other suitable feature) while the individual is performing the bite/chew function required by a given test.

Moreover, the form factor of the mastication measurement device 202 can allow for a short piece of the device to lay parallel along the gum line or molars of the individual being tested without triggering a gag response. As such, the jaw function measurement apparatus 100 affords an opportunity for analysis of statistical significance in chewing function, with placement on the molars or molar ridges, in a 3-dimensional manner.

Thus, by including a set of sensors, measurements can be collected in one or more dimensions (e.g., at least two dimensions reflective of bite and shear). Moreover, such measurements can be collected at multiple locations within the mouth of the data providing data in multiple spatial locations.

In certain implementations, it may be desirable to further include an optional cover 220. The cover can be provided as a reusable detachable cover, or a covering for a device implemented as a one-time use device.

First Example Mastication Measurement Device

Figure 3A:
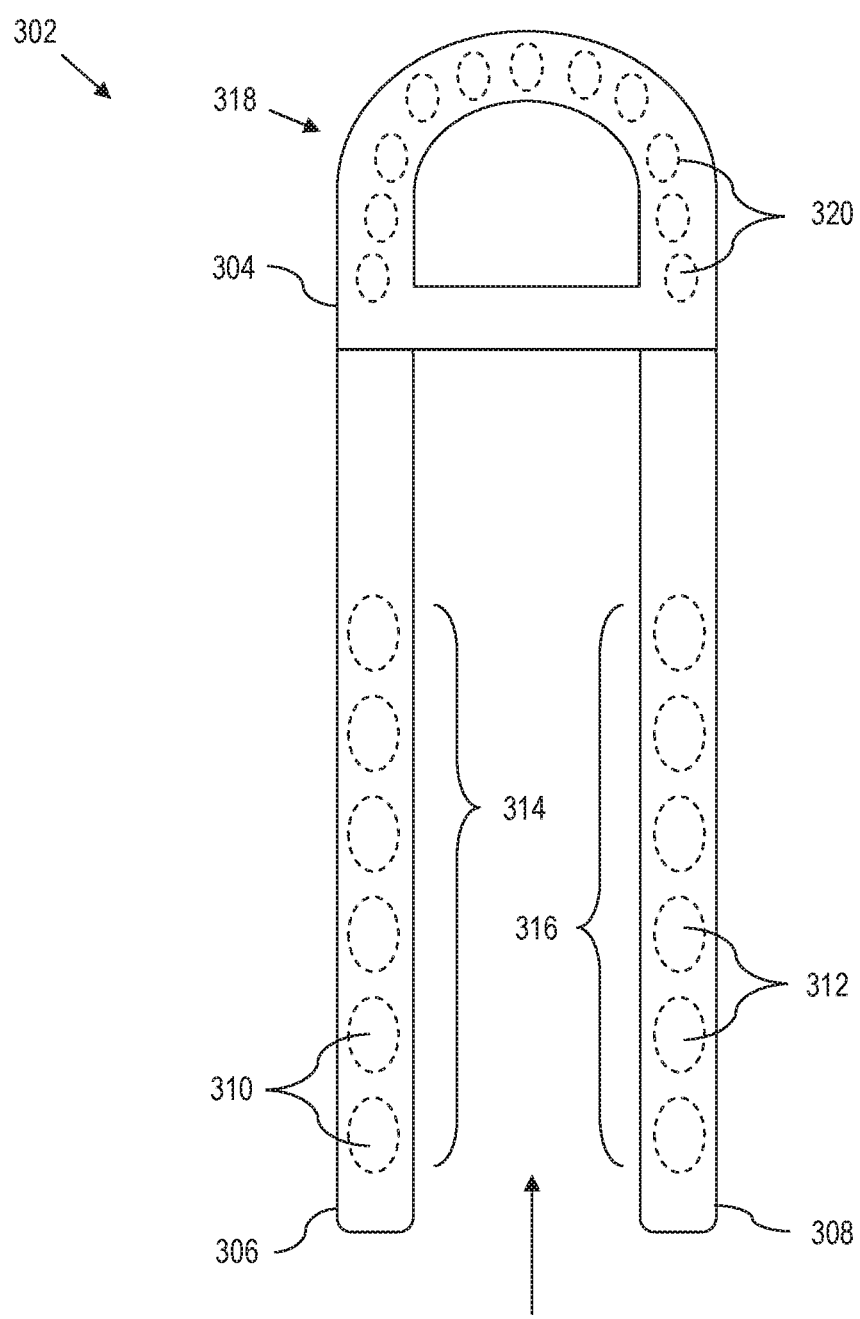
FIG. 3A is a top view of a first example geometry for a mastication measurement device usable with the system of FIG. 1.

Referring to FIG. 3A, a mastication measurement device 302 is illustrated, according to various aspects of the present disclosure herein. Unless otherwise noted, the mastication measurement device 302 is analogous to, and includes the same features of the mastication measurement device 102 of FIG. 1, and/or the mastication device 202 of FIG. 2.

The mastication measurement device 302 comprises a pliable body 304, such as a body having a pliable non-nutritive chewable surface. For instance, the body of the mastication measurement device 302 can be made from durable, non-toxic plastic, which is free of PVC and Phthalates. The body 304 in this example includes a generally U-shaped form. A first "leg" of the U-shaped body defines a first region 306 having a first thickness. Likewise, a second "leg" of the U-shaped body defines a second region 308 having a second thickness. The second region 308 is thicker than the first region 306. By way of example, the first section 306 of the mastication measurement device 302 may be up to 12 millimeters thick, whereas the second section 308 of the mastication measurement device 302 is greater than 12 millimeters. In practical applications, the first region 306 and/or the second region 308 can be implemented as a tube, cuboid, or other shape.

Figure 3B:
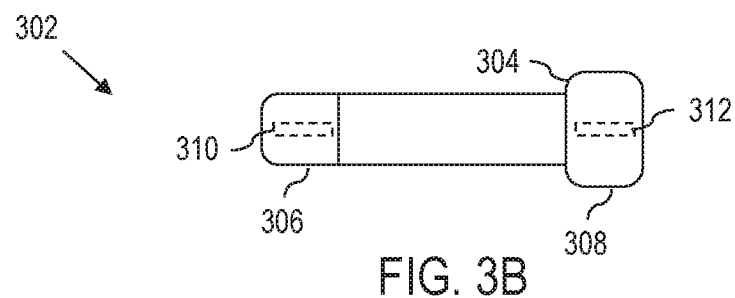
FIG. 3B is an end view of the example mastication measurement device of FIG. 3A.

Referring briefly to FIG. 3B, an end view illustrates that the first region 306 is thinner than the second region 308. Moreover, one or more force sensor(s) 310 is/are within the body 304 within the first section 306, e.g., beneath the non-nutritive chewable surface. Analogously, one or more force sensor(s) 312 is/are within the body 304 within the second region 308 beneath the non-nutritive chewable surface.

In order to collect bite and chewing data, the mastication measurement device 302 can include a plurality of force sensors, as best illustrated in FIG. 3A. At least one force sensor 310 is within the first region 306. Likewise, the mastication measurement device 302 includes at least one force sensor 312 within the second region 308. The force sensor(s) 310 can be the same as, or different from the force sensor(s) 312, e.g., in terms of force sensitivity, threshold, number of sensors, orientation, sensor type, etc. Moreover, in specific embodiments, the first region 306 includes a plurality of sensors 310, and the second section 308 has a plurality of sensors 312. In additional example embodiments, the force sensors can each measure bite force, shear force (transverse to bite force), or a combination thereof.

In another example implementation, the pliable body 304 of the mastication measurement device 302 comprises a non-nutritive chewable surface, at least within the first region 306 and the second region 308. The first region 306 of the pliable body 304 includes a first bite location 314. The first bite location 314 has a length that corresponds to the expected mouth size of a patient chewing on the mastication measurement device 302. The second region 308 of the pliable body 304 has a second bite location 316. The second bite location 316 will typically have a length the same as the first bite location 314. However, the second bite location 316 can be longer or shorter than the first bite location 314. The first bite location 314 and the second bite location 316 can also have the same or different rigidity to provide flexibility in the nature of data collected.

The mastication measurement device 302 also includes a handle 318. The handle 318 can be free of sensors, e.g., to provide a convenient place for the specialist to grasp the device while collecting measurements from a patient. The handle 318 can also include one or more sensors 320, e.g., to capture additional measurements. The sensor(s) 320 can be the same as, or different from the force sensor(s) 310 and or 312, e.g., in terms of force sensitivity, threshold, number of sensors, orientation, sensor type, etc.

The plurality of force sensors 310, 312 are arranged within the pliable body 304 such that at least two of the plurality of force sensors (e.g., are within the first region 306 and at least two of the plurality of force sensors are within the second region 308. Thus, at least one sensor can capture bite force, whereas another sensor can capture shear force. In practice however, any number of force sensors can be used, and an example embodiment may capture both bite and shear forces with the same sensor.

The size, spacing, and number of force sensors in the first region 306 and the second region 308 will be determined by the types of measurements to be performed. For instance, the typical human mouth includes four general types of teeth.

Incisors are in the front and center of the mouth and are used to take bites of food. In an example implementation, any two or more adjacent force sensors can be used to measure bite force, jaw movement, and chewing pattern using incisors. As a further example, sensors can be configured for introduction along the chewing muscles of a patient. This may be useful, for instance, to determine increase effort or recruitment, i.e., to measure muscles such as the masseter, temporalis, and pterygoid.

Canines flank the incisors and are used to rip and tear food apart. As such, to test canines, the force sensors must be positioned to allow the canines on each side of the mouth to be read by one or more corresponding force sensors.

Bicuspids flank the canines and are used to chew and grind food. As such, to test bicuspids, the force sensors must be positioned to allow the bicuspids on each side of the mouth to be read by one or more corresponding force sensors.

Molars are also used for chewing and grinding food. Molars flank the bicuspids. Accordingly, to test molars, the force sensors must be positioned to allow the bite induced by molars on each side of the mouth to be read by one or more corresponding force sensors.

In certain example implementations, only one side of the mouth will be tested at a time. Thus, there can be symmetry in the sensor positioning corresponding to bite locations to allow more flexibility in positioning the bite location with regard to the individual being tested. For instance, a typical length of the sensor region can extend from about 2¼ inches (approximately 5.72 centimeters) to about 3½ inches (approximately 8.89 centimeters).

Thus, the mastication measurement device 302 can be used to objectively measure and collect data regarding bite force, shear rate, fatigue, frequency, motion (and other variables mentioned in greater detail herein) in relation to the molars or molar ridges in a pediatric friendly manner.

In this regard, the particular number and positioning of sensors, the size of the sensor/bite regions, thickness and rigidity can be determined based upon the intended mouth of an average patient that will chew on the mastication measurement device 302. In this regard, there may be a separate mastication measurement device 302 for different age ranges of individuals, e.g., a different mastication measurement device 302 for infants, small children, teenagers, and adults.

In an example embodiment, a second set of force sensors are provided about a curved base of the U-shaped body. This provides an opportunity to align force sensors in a way that fits the form of a typical mouth, e.g., where munch related bite force measurements are to be taken. Alternatively, this portion can define a handle to allow a specialist to hold onto the mastication measurement device 302 during testing.

In yet alternative implementations, one or more regions comprising force sensors can be stair-stepped, graded, continuously change in thickness or otherwise exhibit varying thickness to be able to collect measurements with different jaw positions.

Second Example Mastication Measurement Device

Figure 4A:
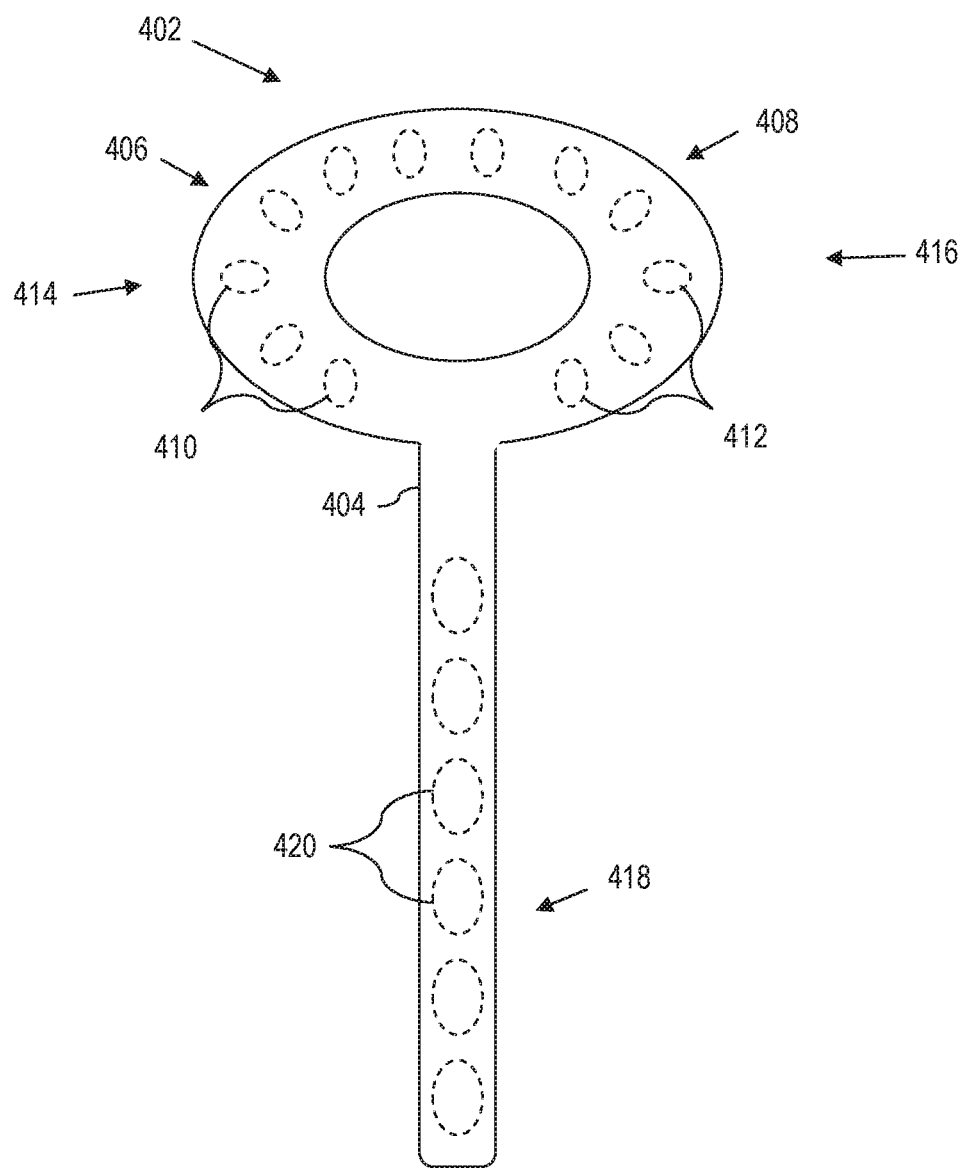
FIG. 4A is a top view of a second example geometry for a mastication measurement device usable with the system of FIG. 1.
Figure 4B:
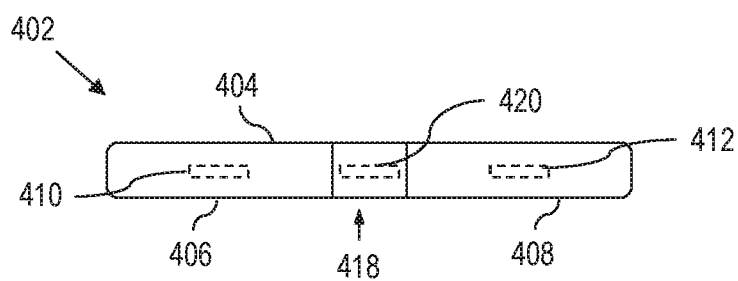
FIG. 4B is an end view of the example mastication measurement device of FIG. 4A.

Referring to FIG. 4A and FIG. 4B, a mastication measurement device 402 is illustrated, according to various aspects of the present disclosure herein. Unless otherwise noted, the mastication measurement device 402 is analogous to, and includes the same features of the mastication measurement device 102 of FIG. 1, and the mastication device 202 of FIG. 2.

The mastication measurement device 402 is also analogous to the mastication measurement device 302 of FIGS. 3A and 3B. As such, like elements are illustrated with like reference numerals 100 digits higher, unless otherwise noted. For instance, a body 404 shown in FIG. 4A is analogous to the body 304 of FIG. 3A, etc. In the example of FIGS. 4A and 4B, the body 404 is generally "key shaped". In an example embodiment, the entire structure of the body is the same thickness, but the body 404 does not need to be the same thickness throughout. Moreover, the entire structure can have the same rigidity or different regions can have different rigidity. Force sensors can be provided throughout, or force sensors can be provided in the "shaft" of the key shaped body. Here, the ring shaped section, can have force sensors therein, e.g., to detect munching patterns, or the ring shaped section can serve as a handle. Alternatively, the shaft can serve as the handle with sensors in the ring shaped portion.

In a manner generally analogous to the example of FIGS. 3A and 3B, the mastication measurement device 402 comprises a pliable body 404, such as a body having a pliable non-nutritive chewable surface. Notably, the ring shaped portion includes a first region 406 having a first thickness. Likewise, the ring shaped portion includes a second region 408 having a second thickness. The second region 408 is thicker than the first region 406. By way of example, the first section 406 of the mastication measurement device 402 may be up to 12 millimeters thick, whereas the second section 408 of the mastication measurement device 402 is greater than 12 millimeters. In another example, the first region 406 and the second region 408 are the same thickness.

Referring briefly to FIG. 4B, an end view illustrates in this example, that the first region 406 is the same thickness as the second region 408. Moreover, one or more force sensor(s) 410 is/are within the body 404 within the first region 406, e.g., beneath the non-nutritive chewable surface. Analogously, one or more force sensor(s) 412 is/are within the body 404 within the second region 408 beneath the non-nutritive chewable surface. The force sensor(s) 410 can be the same as, or different from the force sensor(s) 412, e.g., in terms of force sensitivity, threshold, number of sensors, orientation, sensor type, etc. Moreover, in specific embodiments, the first region 406 includes a plurality of sensors 410, and the second section 408 has a plurality of sensors 412. In additional example embodiments, the force sensors can each measure bite force, shear force (transverse to bite force), or a combination thereof.

In another example implementation, the first region 406 of the pliable body 404 defines a first bite location 414. The first bite location 414 has a length that corresponds to the expected mouth size of a patient chewing on the mastication measurement device 402. The second region 408 of the pliable body 404 defines a second bite location 416. The second bite location 416 will typically have a length the same as the first bite location 414. However, the second bite location 416 can be longer or shorter than the first bite location 414. The first bite location 414 and the second bite location 416 can also have the same or different rigidity to provide flexibility in the nature of data collected.

The mastication measurement device 402 also includes a handle 418. The handle 418 can be free of sensors, e.g., to provide a convenient place for the specialist to grasp the device while collecting measurements from a patient. The handle 418 can also include one or more sensors 420, e.g., to capture additional measurements. The sensor(s) 420 can be the same as, or different from the force sensor(s) 410 and or 412, e.g., in terms of force sensitivity, threshold, number of sensors, orientation, sensor type, etc.

Alternatively, the thickness of the shaft 418 can be different from the thickness of the first section ring shaped portion, e.g., at the first section 406 and/or second section 408. This provides an opportunity for additional measurements because the jaw will be in different positions when biting into each region of the mastication measurement device 402.

In yet alternative implementations, one or more regions comprising force sensors can be stair-stepped, graded, continuously change in thickness or otherwise exhibit varying thickness to be able to collect measurements with different jaw positions.

Third Example Mastication Measurement Device

Figure 5A:
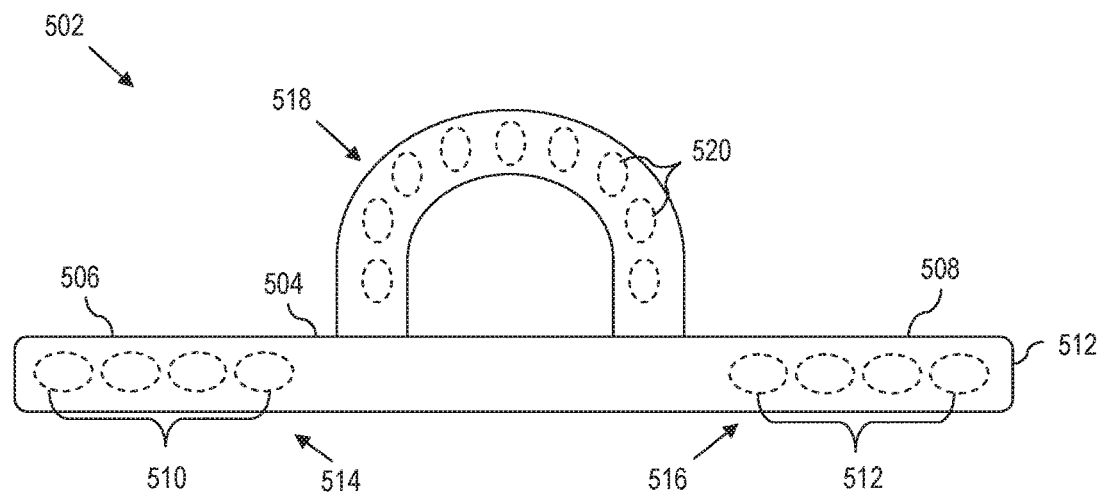
FIG. 5A is a top view of a third example geometry for a mastication measurement device usable with the system of FIG. 1.
Figure 5B:
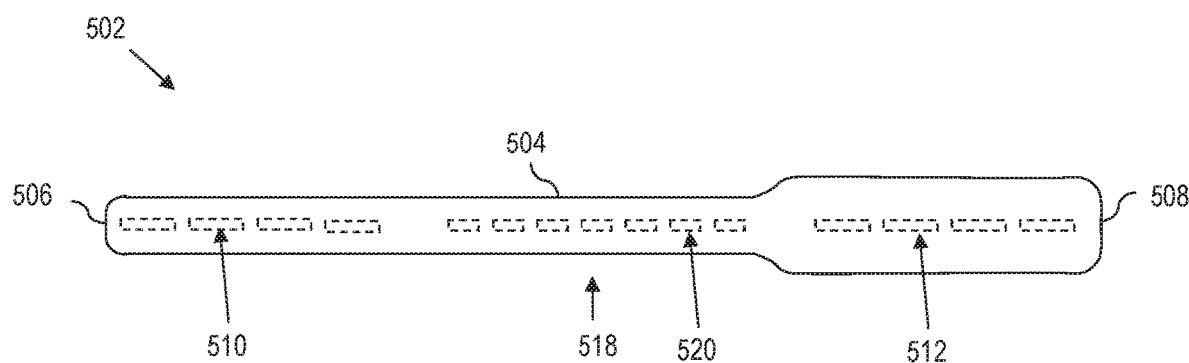
FIG. 5B is an end view of the example mastication measurement device of FIG. 5A.

Referring to FIG. 5A and FIG. 5B, a mastication measurement device 502 is illustrated, according to various aspects of the present disclosure herein. Unless otherwise noted, the mastication measurement device 502 is analogous to, and includes the same features of the mastication measurement device 102 of FIG. 1, the mastication device 202 of FIG. 2.

The mastication measurement device 502 is also analogous to the mastication device 302 of FIGS. 3A and 3B as well as the mastication measurement device 402 of FIGS. 4A and 4B. As such, like elements are illustrated with like reference numerals 100 digits higher (or 200 higher with regard to the embodiment of FIG. 3A, 3B), unless otherwise noted. For instance, body 404 is analogous to body 504, except for geometry, etc.

In the example of FIGS. 5A and 5B, a body 504 is generally "bar shaped" with an optional mouth-shaped handle that extends approximately midway along the length of the bar shape. As noted in greater detail above, the handle can provide a place to hold the device; it can hold sensors, or both. In this regard, the first segment 506 comprises a first half of the bar. Likewise, the second segment 508 comprises a second half of the bar. Moreover, a row of force sensors is in the "handle" of the bar shaped body.

More particularly, in a manner generally analogous to the example of FIGS. 3A and 3B, the mastication measurement device 502 comprises a pliable body 504, such as a body having a pliable non-nutritive chewable surface. Notably, the bar shaped portion includes a first region 506 having a first thickness. Likewise, the bar shaped portion includes a second region 508 having a second thickness. The second region 508 is thicker than the first region 506. By way of example, the first section 506 of the mastication measurement device 502 may be up to 12 millimeters thick, whereas the second section 508 of the mastication measurement device 502 is greater than 12 millimeters. In another example, the first region 506 and the second region 508 are the same thickness.

Referring briefly to FIG. 5B, an end view illustrates in this example, that the first region 506 is relatively thinner compared to the second region 508. Moreover, one or more force sensor(s) 510 is/are within the body 504 within the first region 506, e.g., beneath the non-nutritive chewable surface. Analogously, one or more force sensor(s) 512 is/are within the body 504 within the second region 508 beneath the non-nutritive chewable surface. The force sensor(s) 510 can be the same as, or different from the force sensor(s) 512, e.g., in terms of force sensitivity, threshold, number of sensors, orientation, sensor type, etc. Moreover, in specific embodiments, the first region 506 includes a plurality of sensors 510, and the second section 508 has a plurality of sensors 512. In additional example embodiments, the force sensors can each measure bite force, shear force (transverse to bite force), or a combination thereof.

In another example implementation, the first region 506 of the pliable body 504 defines a first bite location 514. The first bite location 514 has a length that corresponds to the expected mouth size of a patient chewing on the mastication measurement device 502. The second region 508 of the pliable body 504 defines a second bite location 516. The second bite location 516 will typically have a length the same as the first bite location 514. However, the second bite location 516 can be longer or shorter than the first bite location 514. The first bite location 514 and the second bite location 516 can also have the same or different rigidity to provide flexibility in the nature of data collected.

The mastication measurement device 502 also includes a handle 518. The handle 518 can be free of sensors, e.g., to provide a convenient place for the specialist to grasp the device while collecting measurements from a patient. The handle 518 can also include one or more sensors 520, e.g., to capture additional measurements. The sensor(s) 520 can be the same as, or different from the force sensor(s) 510 and or 512, e.g., in terms of force sensitivity, threshold, number of sensors, orientation, sensor type, etc.

The differences in thickness between the regions 506 and 508 provide an opportunity for additional/varied measurements because the jaw will be in different positions when biting into each region of the mastication measurement device 502. In yet alternative implementations, one or more regions comprising force sensors can be stair-stepped, graded, continuously change in thickness or otherwise exhibit varying thickness to be able to collect measurements with different jaw positions.

Fourth Example Mastication Measurement Device

Figure 6A:
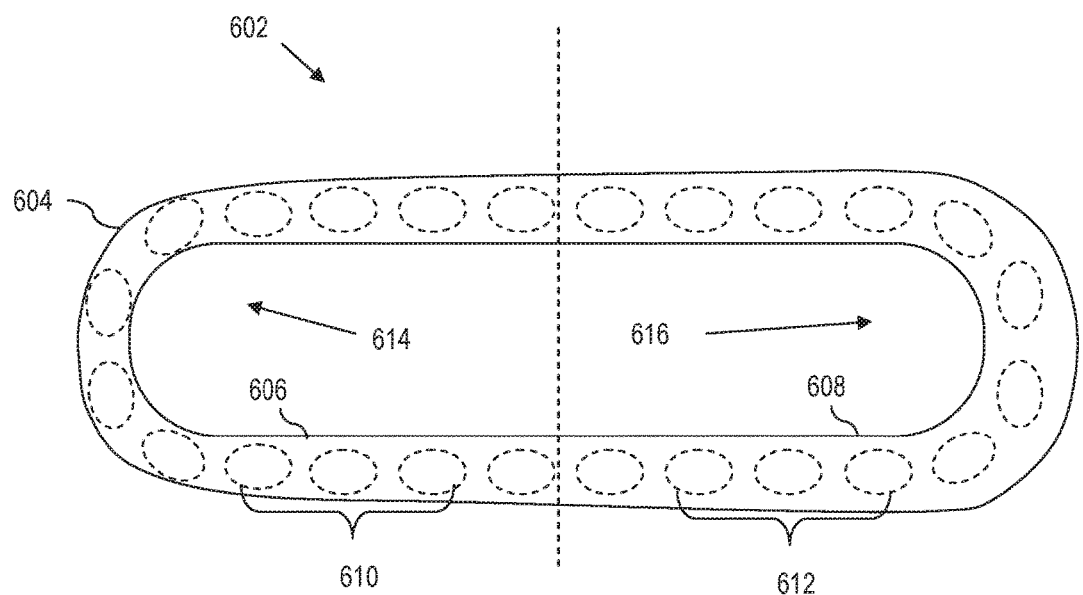
FIG. 6A is a top view of a fourth example geometry for a mastication measurement device usable with the system of FIG. 1.
Figure 6B:
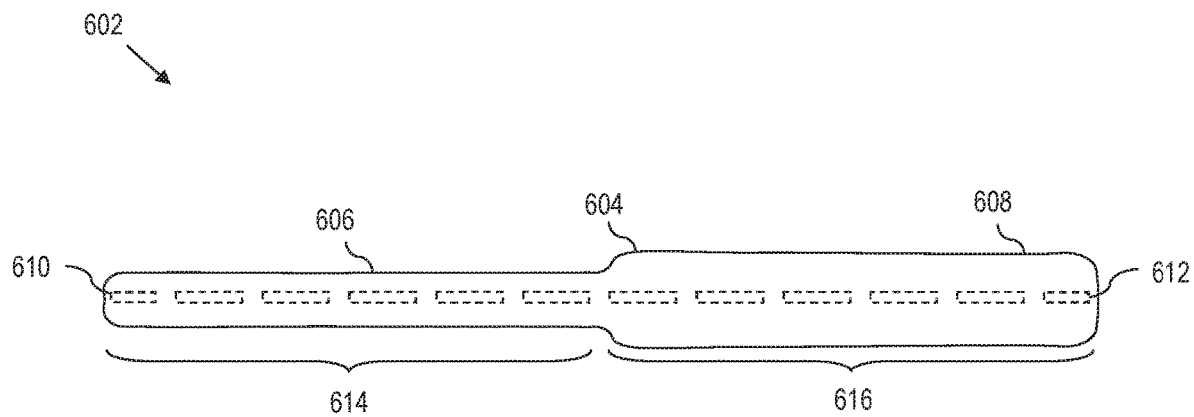
FIG. 6B is an end view of the example mastication measurement device of FIG. 6A.

Referring to FIG. 6A and FIG. 6B, a mastication measurement device 602 is illustrated, according to various aspects of the present disclosure herein. Unless otherwise noted, the mastication measurement device 602 is analogous to, and includes the same features of the mastication measurement device 102 of FIG. 1, the mastication device 202 of FIG. 2, the mastication device 402 of FIGS. 4A and 4B.

Moreover, the mastication measurement device 602 is analogous in many respects to the mastication measurement device 302 of FIG. 3A and FIG. 3B, the mastication measurement device 402 or FIG. 4A and FIG. 4B, the mastication measurement device 502 of FIG. 5A and FIG. 5B, or a combination thereof. As such, like elements are illustrated with like reference numerals 100 digits higher from FIG. 5A, FIG. 5B, (or 200 digits higher from FIG. 4A, 4B, or 300 digits higher from FIG. 3A, 3B) except where noted.

Referring to FIGS. 6A and 6B generally, analogous to the example of FIGS. 3A and 3B, the mastication measurement device 602 comprises a pliable body 604, such as a body having a pliable non-nutritive chewable surface. Notably, the generally oval shaped portion includes a first region 606 having a first thickness. Likewise, the generally oval shaped portion includes a second region 608 having a second thickness. Here, the first segment 606 comprises a semicircle around the oval portion. Likewise, the second segment 608 comprises a semicircle around the opposite half of the oval portion. The second region 608 is thicker than the first region 606. By way of example, the first section 606 of the mastication measurement device 602 may be up to 12 millimeters thick, whereas the second section 608 of the mastication measurement device 602 is greater than 12 millimeters. In another example, the first region 606 and the second region 608 are the same thickness.

Referring briefly to FIG. 6B, an end view illustrates in this example, that the first region 606 is relatively thinner compared to the second region 608. Moreover, one or more force sensor(s) 610 is/are within the body 604 within the first region 606, e.g., beneath the non-nutritive chewable surface. Analogously, one or more force sensor(s) 612 is/are within the body 604 within the second region 608 beneath the non-nutritive chewable surface. The force sensor(s) 610 can be the same as, or different from the force sensor(s) 612, e.g., in terms of force sensitivity, threshold, number of sensors, orientation, sensor type, etc. Moreover, in specific embodiments, the first region 606 includes a plurality of sensors 610, and the second section 608 has a plurality of sensors 612. In additional example embodiments, the force sensors can each measure bite force, shear force (transverse to bite force), or a combination thereof.

In another example implementation, the first region 606 of the pliable body 604 defines a first bite location 614. The first bite location 614 has a length that corresponds to the expected mouth size of a patient chewing on the mastication measurement device 602. The second region 608 of the pliable body 604 defines a second bite location 616. The second bite location 616 will typically have a length the same as the first bite location 614. However, the second bite location 616 can be longer or shorter than the first bite location 614. The first bite location 614 and the second bite location 616 can also have the same or different rigidity to provide flexibility in the nature of data collected.

In yet alternative implementations, one or more regions comprising force sensors can be stair-stepped, graded, continuously change in thickness or otherwise exhibit varying thickness to be able to collect measurements with different jaw positions.

Example Parameters

Referring to FIG. 7, a table 700 illustrates various example parameters that can be captured by the jaw function measurement device described herein, e.g., including the hardware described with reference to FIG. 1. For instance, a first parameter 702 can record whether an individual is incapable or unwilling to bite. This can be accomplished by initiating a bite test and timing out over a predetermined duration before recording a force measurement above a predetermined threshold.

A second parameter 704 can record bite force, i.e., the force applied in a bite. This can be accomplished for instance, by separately recording force measurements out of each sensor, by averaging across multiple sensors, by averaging over multiple bite samples, etc. In this regard, signal conditioning including the use of thresholds, filters, duration windows and other processing techniques can be utilized to compute the result.

A third parameter 706 can record a frequency measurement, e.g., by detecting distinct bites, which can include a measurement of the time between bites, e.g., as a frequency/frequency fluctuation, trend, etc. Again, thresholds and other techniques can be used to discriminate bit bite signals. Here, counted bites are measured over a predetermined time period. In certain examples, detected bites can be further binned, e.g., based upon bite force or range of bite forces, allowing multi-dimensional readings to be achieved.

A fourth parameter 708 can record duration, e.g., the time measure of the duration of a single bite (how long force is applied per bite). Here, a first bite measure, e.g., minimum bite force threshold triggers the initiation of the bite, and a release threshold indicates that the bite has let go. The resulting output can be a measure (e.g., duration) or an envelope tracing bite force as a function of time.

A fifth parameter 710 can measure endurance, i.e., how long in time (or a count of how many) repeated bites are recorded. Again, consistent with the examples above, thresholds, timers, etc. can be used to capture, potentially multi-dimensional data.

A sixth parameter 712 can measure shear force (e.g., force transverse to bite force). Again, consistent with the examples above, thresholds, timers, etc. can be used to capture, potentially multi-dimensional data.

Moreover, additional information such as a seventh parameter 714 records jaw position can be recorded, e.g., as a function of the thickness of the bite location of the mastication measurement device.

Also, an eighth parameter 716 can record the hardness/rigidity of the bite region of the mastication measurement device.

Figure 8:
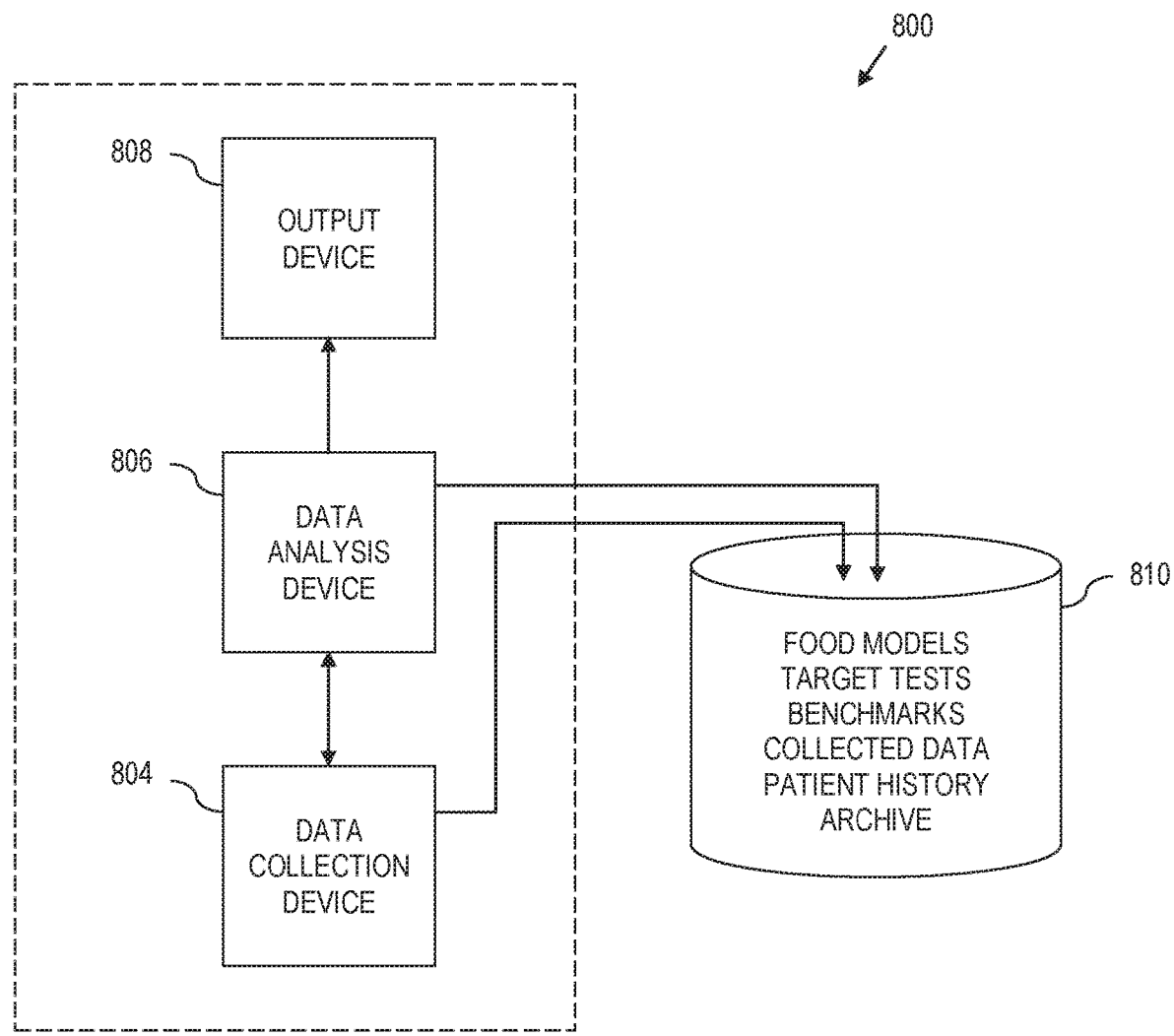
FIG. 8 is a block diagram of a jaw function measurement apparatus coupled to a data source to obtain tests, analyze results, and store test measurements.

Referring to FIG. 8, a portion of an analysis device illustrates a data collection device 804 in data communication with a data analysis device 806. The data analysis device 808 is in data communication with an input/output device 808. These components are analogous to corresponding components of FIG. 1. However, as illustrated in FIG. 8, the data analysis device 806 and/or the data collection device 804 can communicate with a data source 810 (e.g., one or more databases). These databases can store information used for data analysis. For instance, the data source 810 can store one or more food models (such as a soft solid model (e.g., associated with canned fruit or vegetable/pasta); a sandwich model (e.g., which measures for relatively wider jaw excursion); a solid model (e.g., associated Steak/Raw vegetable) (shearing/bite force and increase duration of chewing cycle). A food model is a set of parameter values that match food types to one or more of the parameters of FIG. 7. For instance, food ABC requires a force of X and Y repetitive chews. In finer levels of granularity, the food models can account for whole food items vs. bites of the food item, e.g., a whole cracker vs. a bite of a cracker to account for differences based upon the quantity and/or size of food to be chewed. This data can be used to compare against actual measured test results to issue pass/fail assessments for food types.

Another type of data that can be stored in the data source 810 is jaw function tests. A target test is a test specification that identifies which parameters to record (e.g., of those identified in FIG. 7 or otherwise herein, which food model to use, which size measurement device to use, which hardness/rigidity of measurement device to use, etc. to properly specify a jaw function to be measured.

Yet another type of data that can be stored in the data source 810 is benchmark data. Benchmark data establishes measurable parameters to compare actual measured test results against. This provides the ability to assess percentages of development, to stratify results, etc.

Still further, another type of data that can be stored in the data source 810 is the actual measurement results and testing conditions themselves.

Yet further, another type of data that can be stored in the data source 810 is archive data, or actual measurement data across a plurality of individuals.

The data source 810 can also store images collected from a camera, video capture device, audio capture device or other sensor, e.g., from a data capture device (110 FIG. 1).

Still further, the data source 810 can store computer code that executes a wizard. The wizard can guide a specialist, e.g., via graphics and images output via the output device 808 to demonstrate the proper use of the mastication measurement device. The wizard can also trigger the data collection device to start recording data, e.g., according to a test associated with a predetermined food model, target test, etc. As such, a guided examination can be carried out in a way that consistently and accurately collects results that improve the quality of the historical records.

Figure 9:
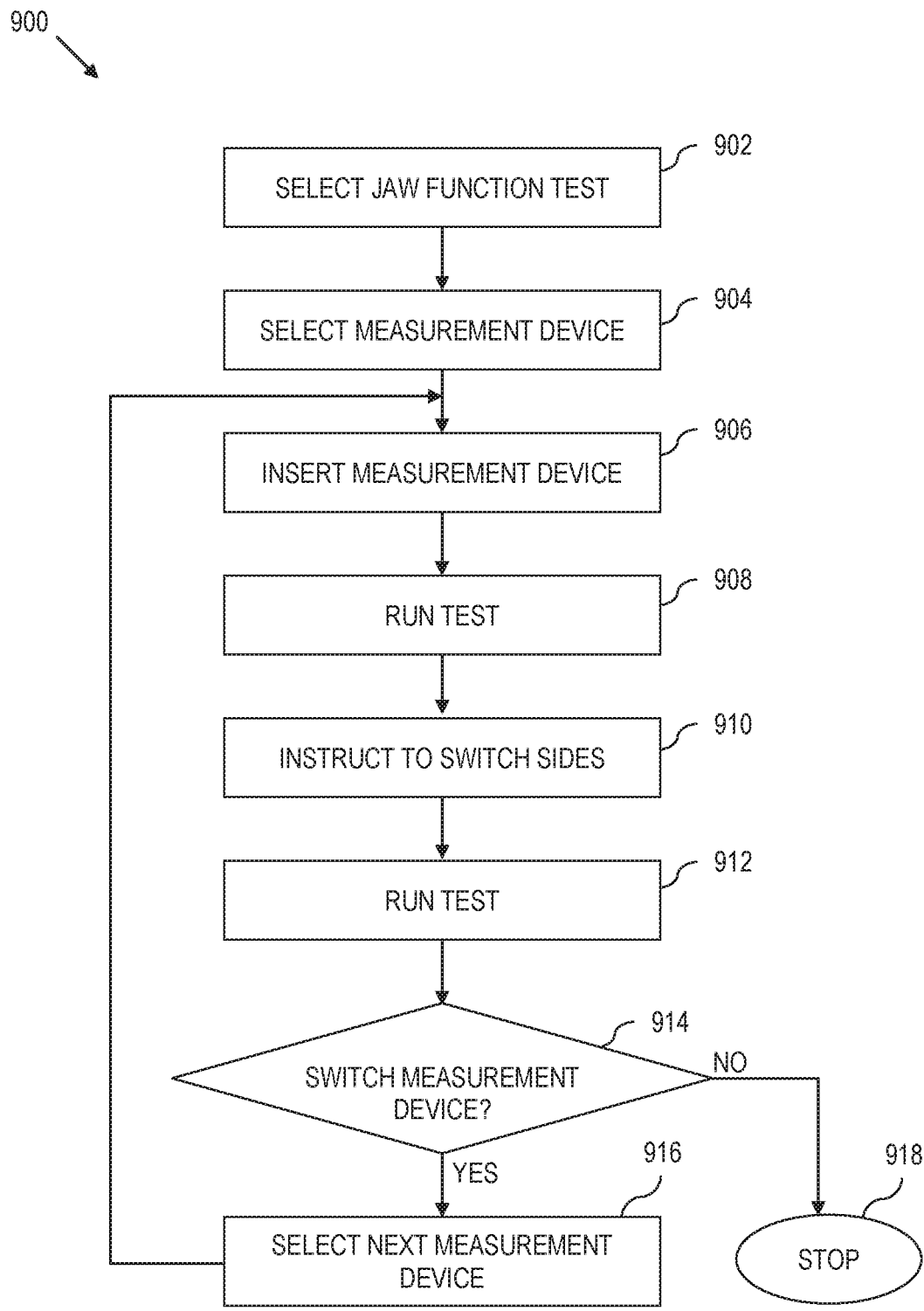
FIG. 9 is a method of assessing jaw function.

Referring to FIG. 9, a method 900 of testing jaw function is provided.

At 902, the method comprises selecting a jaw function test. Jaw function tests are described with regard to FIG. 8. For example, a test may probe the ability to bite through a dissolvable cracker to help determine readiness for diet progression as skills emerge. e.g., based upon a predetermined food model. The test can also be selected to measure one or more predetermined parameters, or the test may be triggered by a control application, e.g., a guided wizard or other software At 904, the method comprises specifying a measurement device. Otherwise, a specialist will select a measurement device at 904. The measurement device will establish the thickness, rigidity, combination thereof, or other parameters as set out herein. The thickness will generally simulate the size of food being simulated, e.g., cracker thickness vs. sandwich thickness, etc. The rigidity simulates the food texture, e.g., soft bread vs. cracker, etc.

At 906, the method comprises inserting the measurement device into the mouth of the individual being tested, typically on one side of the mouth, e.g., along the molars or molar ridge.

At 908, the method comprises running the test according to the enabled parameters, conditions, and other variables associated with the test. For instance, a test that only requires one bite will execute differently from a test that requires chewing frequency, duration, endurance, a combination thereof, etc. to be measured. Thus, the specific test dictates which of the parameters is measured against, and how that test is performed.

During testing, a specialist may need to verbally and visually cue a child to bite. As the child bites, the specialist can observe approximation of dentition, contact with measurement device (simulating food such as a cracker), observance of breakage (size of bite obtained/scattering of food). Should a child not respond with biting function, the specialist can offer stimulation to the upper and lower molar ridges/molars to facilitate a spontaneous bite function. The specialist can also observe spontaneous response representative of food breakage such as emerging munching pattern, hypergag response, hyposensitive response, or attempt to wipe food from oral cavity.

At 910, the method comprises instructing the specialist to move the measurement device to the opposite side of the mouth.

At 912, the method comprises repeating the test.

At 914, the method comprises making a decision as to whether a different measurement device is required to continue, e.g., to assess a different aspect of jaw function. This may comprise switching to a thicker or thinner measurement device (to assess the parameters at a different jaw angle), switching to a measurement device with a different rigidity/hardness (to test willingness/ability to bite into harder/softer substances), a combination thereof, etc.

If there is a need to conduct further testing, the method selects the next measurement device at 918, and loops back to 906.

If there is no need to perform other measurements, the method ends at 920.

As noted in greater detail with reference to FIG. 1, the method 900 may also optionally include capturing video or information from one or more additional devices to synchronize with the bite force data.

General Observations

Referring to the figures generally, the jaw function measurement apparatus defines a pliable bite force device that is used measure bite force, chewing capability, chewing and biting patterns, and other functions. Moreover, unlike previous devices, the dynamic process of 3-dimensional repetitive chewing can be assessed. In this regard, data from the force sensors can be used to establish a graded analysis of baseline jaw function in typical and atypical developments to further promote evaluation and treatment parameters of mastication and to reduce choking risk.

For instance, measurements collected by the jaw function measurement apparatus can be used by a specialist to assess conditions such as: a lack of skill to bite through any food; an inability to bite with sufficient force to break a food; fatigue of muscle function resulting in an inability to sustain repetitive chewing to manipulate the food, a reduced muscular coordination with jaw slide, tremor, reduced saliva management and/or refusal to continue eating; coordination and motion of jaw during bolus manipulation and food deformation, and other dysfunctions.

For instance, due to the number, size, and spacing of the bite force sensors, and due to the thickness of the body at the location of various bite force sensors, the jaw function measurement apparatus 100 of FIG. 1 can be utilized to determine quantifiable bite force, bite frequency, bite shear, shear rate, jaw endurance, fatigue, jaw stability, jaw motion (horizontal, vertical, rotary, diagonal) from at least two jaw gradation positions. Slightly widening the diameter may help adjust for mastication of wider foods (for example, the first region may simulate the thickness of a thin cracker, whereas the second region may be thicker, e.g., to approximate the thickness of a typical sandwich.

Also, as noted above, bite force measurement values can be augmented with data from a different domain, e.g., camera data. The use of camera data can be used, for instance, to detect, predict, or otherwise derive forces that correspond with food breakage and deformation. Exploration of facial kinematics can also be utilized to enhance measurements for baseline data.

The jaw function measurement apparatus 100 can be utilized for instance, to establish a baseline for evaluation. This allows progress over time to be accurately captured. Moreover, the jaw function measurement apparatus 100 can be used to establish benchmark levels of performance across populations so that objective evaluations of patients and patient development in biting and chewing skills can be assessed. Still further, the jaw function measurement apparatus 100 can be used to establish and/or evaluate discharge criteria, evaluate pre and post stimulation treatments, etc.

This vast amount of new information that can be collected, allows the specialist to assess, re-assess and determine baseline data for development of chewing function from an early munching pattern appropriate for exploration of textured purees or dissolvable crunchy foods to a more mature rotary chew appropriate for table foods requiring significant repetitive chewing such as meats.

Moreover, because of the arrangement of the sensors, the mastication measurement device can be used for quantifying biting/chewing and jaw function bilaterally to better determine asymmetrical function, horizontal sliding of the jaw for shearing, unilateral weakness impacting safety with chewing foods of increasing challenge and/or maladaptive compensatory motor/sensory responses to inefficient chewing function. In conjunction with evaluation of food properties, it may be used to assist physicians, clinicians and families determine safest diet level recommendations as chewing skills emerge. It may also be used to offer information for consistency of care across settings such as daycare, schools, community outings and home to enhance safety at meal times. This concept affords significant advantages for the analysis of typical and atypical chewing development. Also, the device can provide objective data of chewing and feeding function across disciplines (speech language pathology, occupational therapy, etc.) for standardization of care and best evidenced based practices.

The specific geometry of the mastication measurement device can be child-friendly (visually/tactilely) and is applicable for repetitive functional chewing activity.

Yet further, the mastication measurement device can include placement designations (chewing surface), e.g., to indicate where to place the molars or molar ridges of the patient under evaluation.

Example Hardware to Implement the Processing Devices of FIG. 1

Figure 10:
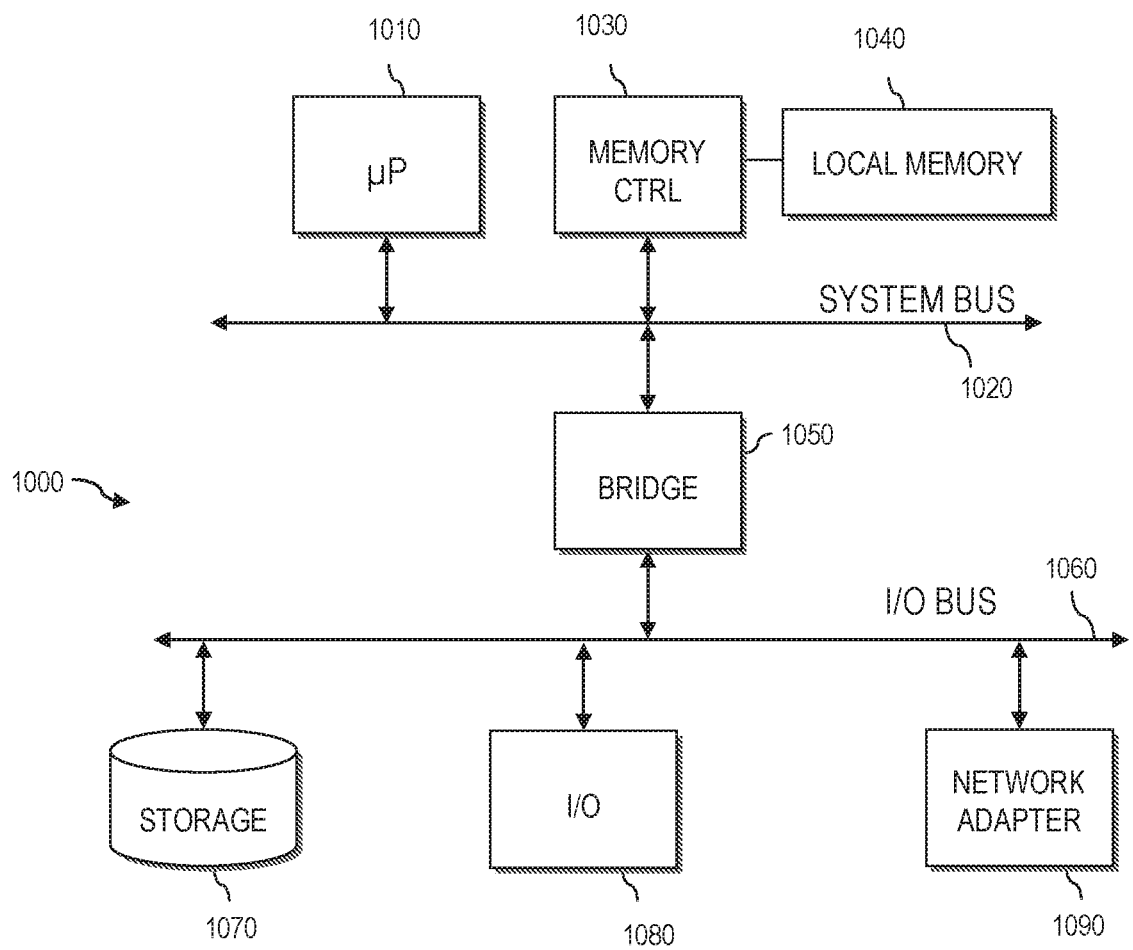
FIG. 10 is a block diagram of a computer system having a computer readable storage medium for implementing functions according to various aspects of the present disclosure as described in greater detail herein.

Referring to FIG. 10, a block diagram of a data processing system is depicted in accordance with the present disclosure. Data processing system 1000 may comprise a symmetric multiprocessor (SMP) system or other configuration including a plurality of processors 1010 connected to system bus 1020. Alternatively, a single processor 1010 may be employed. Also connected to system bus 1020 is memory controller/cache 1030, which provides an interface to local memory 1040. An I/O bus bridge 1050 is connected to the system bus 1020 and provides an interface to an I/O bus 1060. The I/O bus may 1060 be utilized to support one or more devices such storage 1070 (including removable storage medium devices, a computer usable storage medium having computer usable program code embodied thereon, etc). The I/O bus 1060 may also support input/output devices 1080 and a network adapter 1090. The computer usable program code may be executed to implement, control or interact with any aspect of the present disclosure, for example, to implement any aspect of any of the methods and/or system components illustrated in FIGS. 1-9.

In implementing computer aspects of the present disclosure, any combination of computer-readable medium may be utilized. The computer-readable medium may be a computer readable signal medium, or a computer-readable storage medium. Moreover, a computer-readable storage medium may be implemented in practice as one or more distinct mediums.

A computer-readable signal medium is a transitory propagating signal per se. A computer-readable signal medium may include computer readable program code embodied therein, for example, as a propagated data signal in baseband or as part of a carrier wave. However, specifically, a computer-readable signal medium does not encompass a computer-readable storage medium.

A computer-readable storage medium is a tangible device/hardware that can retain and store a program (instructions) for use by or in connection with an instruction execution system, apparatus, or device, e.g., a computer or other processing device set out more fully herein. Notably, a computer-readable storage medium does not encompass a computer-readable signal medium. Thus, a computer readable storage medium, as used herein, is not to be construed as being transitory signals per se, such as radio waves or other freely propagating electromagnetic waves through a transmission media.

Specific examples (a non-exhaustive list) of the computer-readable storage medium include the following: a hard disk, a random access memory (RAM), a read-only memory (ROM), an erasable programmable read-only memory (EPROM), Flash memory, or any suitable combination of the foregoing. In particular, a computer-readable storage medium includes computer-readable hardware such as a computer-readable storage device, e.g., memory. Here, a computer-readable storage device and computer-readable hardware are physical, tangible implementations that are non-transitory.

By non-transitory, it is meant that, unlike a transitory propagating signal per se, which will naturally cease to exist, the contents of the computer-readable storage device or computer-readable hardware that define the claimed subject matter persists until acted upon by an external action. For instance, program code loaded into random access memory (RAM) is deemed non-transitory in that the content will persist until acted upon, e.g., by removing power, by overwriting, deleting, modifying, etc.

Moreover, since hardware comprises physical element(s) or component(s) of a corresponding computer system, hardware does not encompass software, per se.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A jaw function measurement apparatus comprising:
a mastication measurement device comprising:
  a pliable body defining a first region having at least one force sensor, and a second region having at least one force sensor, wherein the first region and the second region differ in thickness so as to require a jaw of an individual being evaluated by a given test to initiate an onset of a bite/chew function with the jaw in different angular positions, thus providing measurement data defining a gradation of jaw function measurements; and
  a position for an evaluator to hold and to maintain control of the mastication measurement device while the individual is performing the bite/chew function required by the given test so as to measure force by incisors, and at least one of canines, bicuspids, and molars; and
a data collection device having circuitry in data communication with the mastication measurement device that collects and records the measurement data from the mastication measurement device;
wherein:
  a processor in data communication with the data collection device assesses chewing function of the individual by evaluating the measurement data across the gradation of jaw function measurements; and
  an output device outputs the chewing function assessed by the processor.

2. The jaw function measurement apparatus of claim 1, wherein:
the at least one force sensor in the first region comprises a first plurality of force sensors arranged within the pliable body to collectively measure bite force and shear force transverse to the bite force; and
the at least one force sensor in the second region comprises a second plurality of force sensors arranged within the pliable body to collectively measure bite force and shear force transverse to the bite force.

3. The jaw function measurement apparatus of claim 2, wherein at least one force sensor comprises a vibration sensor.

4. The jaw function measurement apparatus of claim 1, wherein the mastication measurement device further comprises:
a first region having a first rigidity, and a second region having a second rigidity different from the first rigidity sufficient to define two distinct measurements of chewing capability.

5. The jaw function measurement apparatus of claim 1, wherein:
the first region has a first rigidity, and a second region has a second rigidity different from the first rigidity.

6. The jaw function measurement apparatus of claim 5, wherein at least one force sensor measures bite force and at least one sensor measures shear force transverse to the bite force.

7. The jaw function measurement apparatus of claim 1, wherein:
the pliable body of the mastication measurement device comprises a non-nutritive chewable surface;
the first region of the pliable body has a first bite location;
the second region of the pliable body has a second bite location; and
at least two force sensors are within the first region and at least two force sensors are within the second region.

8. The jaw function measurement apparatus of claim 1, wherein:
the second region of the mastication measurement device is thicker than the first region of the mastication measurement device; and
a thickness of the second region is greater than 12 millimeters.

9. The jaw function measurement apparatus of claim 1, wherein the mastication measurement device includes a tube that contains the plurality of sensors.

10. The jaw function measurement apparatus of claim 1, wherein the mastication measurement device comprises graded widths, each graded width having at least one sensor therein, each graded width configured to assess a different jaw position.

11. The jaw function measurement apparatus of claim 1, wherein the data collection device captures a series of bite measurements so as to record bite force, and at least one of bite frequency, bite shear, jaw endurance, jaw stability, and jaw motion.

12. The jaw function measurement apparatus of claim 1, wherein:
the data collection device captures a series of bite measurements so as to record bite force, and at least one of bite frequency, bite shear, jaw endurance, jaw stability, and jaw motion in each of the first region and the second region.

13. The jaw function measurement apparatus of claim 1 further comprising:
   a database that stores food models, each food model corresponding a food type to particular values of measurable parameters that can be recorded by the mastication measurement device, a particular food model being selectable;
   wherein the processor is configured to compare actual measured values against the values stored in the selected food model to assess jaw function performance.

14. The jaw function measurement apparatus of claim 1 further comprising:
   a database that stores jaw function test specifications that are read out and executed by the processor to specify which of a set of parameters are required to be measured during a test.

15. The jaw function measurement apparatus of claim 1 further comprising:
   a database that stores benchmarks, each benchmark associating particular values of measurable parameters that can be recorded by the mastication measurement device;
   wherein the processor is configured to compare actual measured values against a selected benchmark to assess jaw function performance.

16. The jaw function measurement apparatus of claim 1 further comprising:
   a database that stores:
     food models, each food model corresponding a food type to particular values of measurable parameters that can be recorded by the mastication measurement device, a particular food model being selectable;
     jaw function test specifications that are read out and executed by the processor to specify which of a set of parameters are required to be measured during a test; and
     benchmarks, each benchmark associating particular values of measurable parameters that can be recorded by the mastication measurement device;
   wherein the processor is configured to compare actual measured values against the values stored in a selected food model or a selected benchmark to assess jaw function performance.

17. The jaw function measurement apparatus of claim 1, wherein the pliable body further comprises a temperature generating sensor that can generate at least one of cold or heat.

18. The jaw function measurement apparatus of claim 1 further comprising a data capture device that is further coupled to the data collection device.

19. A jaw function measurement apparatus comprising:
   a mastication measurement device comprising:
     a pliable body defining a first region having at least one force sensor, and a second region having at least one force sensor, wherein the first region and the second region differ in thickness so as to require a jaw of an individual being evaluated by a given test to initiate an onset of a bite/chew function with the jaw in different angular positions, thus providing measurement data defining a gradation of jaw function measurements; and
     a position for an evaluator to hold and to maintain control of the mastication measurement device while the individual is performing a bite/chew function required by the given test so as to measure force by incisors, and at least one of canines, bicuspids, and molars; and
   a processor in data communication with the mastication measurement device that is operatively programmed to:
     collect and record the measurement data from the mastication measurement device;
     assess chewing function of the individual by evaluating the measurement data across the gradation of jaw function measurements; and
     output the assessed chew function.

* * * * *